(12) United States Patent
LeJeune et al.

(10) Patent No.: US 6,759,220 B1
(45) Date of Patent: Jul. 6, 2004

(54) ENZYME-CONTAINING POLYURETHANES

(75) Inventors: Keith E. LeJeune, Pittsburgh, PA (US); Alan J. Russell, Wexford, PA (US)

(73) Assignee: Agentase, LLC, Pittsburgh, PA (US)

( * ) Notice: Subject to any disclaimer, the term of this patent is extended or adjusted under 35 U.S.C. 154(b) by 0 days.

(21) Appl. No.: 09/441,592

(22) Filed: Nov. 17, 1999

(51) Int. Cl.$^7$ .................. C12N 11/18; C12N 11/08; C12N 11/04
(52) U.S. Cl. .................. 435/175; 435/180; 435/182
(58) Field of Search ................ 435/174, 176, 435/177, 180, 182, 175

(56) References Cited

U.S. PATENT DOCUMENTS

| | | | |
|---|---|---|---|
| 3,928,138 A | 12/1975 | Wood et al. | |
| 3,929,574 A | 12/1975 | Wood et al. | ......... 435/43 |
| 4,098,645 A | 7/1978 | Hartdegen et al. | ......... 435/174 |
| 4,195,127 A | 3/1980 | Hartdegen et al. | ......... 435/174 |
| 4,250,267 A | 2/1981 | Hartdegen et al. | ......... 435/317 |

OTHER PUBLICATIONS

LeJeune, et al., Biotechnology & Bioengineering, vo. 64, No. 2 Jul. 20, 1999, pp. 250–254.*

LeJeune et al., Biotechnology & Bioengineering, vol. 51, No. 4, Aug. 20, 1996, pp. 450–457.*

LeJeune, et al., Biotechnology & Bioengineering, vol. 54, No. 2 Apr. 20, 1997, pp. 105–141.*

Havens, et al., Ind. Eng. Chem. Res. vol. 32, No. 10, 1993, pp. 2254–2258.*

Havens, P. L., and Rase, H.F., "Reusable Immobilized Enzyme/Polyurethane Sponge for Removal and Detoxification of Localized Organophosphate Pesticide Spills," Ind. Eng. Chem. Res., 32:10, 2254–2258 (1993).

Storey, K.B. et al., "Immobilization of Amyloglucosidase Using Two forms of Polyurethane Polymer," Applied Biochemistry and Biotechnology, vol. 23, 221–236 (1990).

Gordon, R.K. et al., "Organophophate Skin Decontamination Using Immobilized Enzymes," Chemico–Biological Interactions, 119–120, 463–470 (1999).

van de Velde, F. et al., "Improved Operational Stability of Peroxidases by Coimmobilizatiojn with Glucose Oxidase," Biotechnology and Bioengineering, 69:3, 286–291 (2000).

LeJeune, K.E. et al., "Increasing the Toleerance of Organophosphorus Hydrolase to Bleach," Biotechnology and Bioengineering, 64:2, 250–254 (1999).

* cited by examiner

*Primary Examiner*—David M. Naff
(74) *Attorney, Agent, or Firm*—Craig G. Cochenour; Buchanan Ingersoll PC (57) ABSTRACT

A method of increasing loading of active enzyme immobilized in a polyurethane polymer including the steps of: synthesizing the polyurethane polymer in a reaction mixture containing water and enzyme; and including a sufficient amount of a surfactant in the reaction mixture to increase enzyme activity at an enzyme loading.

8 Claims, 5 Drawing Sheets

Figure 1. Reaction schematic of biopolymer synthesis.

Figure 2. Surfactant effect on catalytic activity of subtilsin polymers.

Figure 3. Surfactant effects on activity of urease polymers.

Figure 4. Effect of F-68 surfactant concentration on subtilisin-polymer activity.

Figure 5. Effect of using different surfactants on subtilisin-polymer activity.

ENZYME-CONTAINING POLYURETHANES

FIELD OF THE INVENTION

The present invention relates to enzyme-containing polyurethanes, and, especially, to enzyme-containing polyurethanes of relatively high enzyme loading and relatively high catalytic (enzyme) activity.

BACKGROUND OF THE INVENTION

It has been known for some time that one can incorporate proteins within polyurethane polymers during polymer synthesis. For example, U.S. Pat. Nos. 3,928,138, 3,929,574, 4,098,465, 4,195,127, and 4,250,267 describe enzymes bound within a hydrophilic polyurethane polymer. Although enzyme activity was evident in those polymers, no attempt was made to quantify the degree of enzyme activity within the polymers.

Academics have more recently begun to revisit the synthesis of enzymatic polyurethane. For example, Dias et al. assessed the performance of lipase incorporated within polyurethane foams. Dias, S. F., Vilas-Boas, L., Cabral, J. M. S., and Fonseca, M. M. R., *Biocatalysis*, 5, 21 (1991). That study described the synthesis of enzymatic polymers without the use of additives, enzyme stabilizers, or enzyme pre-modification. Enzyme concentration within the polymers was varied over a broad range in the course of this study. Those studies indicated an apparent reduction in enzyme activity retention at high enzyme loading (for example, greater than 0.1 weight percent).

Storey et al described the immobilization of amyloglucosidase enzyme within several types of crosslinked polyurethane matrices Storey, K. B., Duncan, J. A., Chakrabarti, J. A., *Appl. Biochem. Biotechnol.* 23, 221 (1990). The enzyme concentrations employed in that study were relatively dilute and the use of additives or other non-essential components was not explored.

Recent studies of general polyurethane synthesis (irrespective of incorporation of enzyme therein) have shown that incorporation of a surfactant in the reaction mixture can lead to desirable physical properties of the polyurethane polymer product. It is believed that surfactants stabilize the carbon dioxide bubbles that are formed during synthesis and are responsible for foaming. For example, certain surfactants have been found to promote the creation of small carbon dioxide bubble, resulting in formation of a polymer product having a morphology similar to a fabric. Other surfactant have been found to promote relatively large carbon dioxide bubbles, resulting in a polymer product having a morphology similar to a sponge. Given the control that surfactants enable over the physical/morphological characteristics of polyurethanes, suppliers of polyurethane prepolymer typically recommend that surfactant be added to a polyurethane reaction mixture.

Thus, recent studies of the synthesis of enzyme-containing polyurethanes have employed surfactants to alter/control the physical properties of the resultant polymers. For example, a number of studies describe the immobilization of organophosphorus hydrolase using a polyurethane polymer synthesis strategy in which a variety of non-ionic surfactants were used as additives to alter the physical properties polymers. Havens, P. L., Rase, H. F., *Ind. Eng. Chem. Res.*, 32, 2254 (1993); LeJeune, K. E., Swers, J. S., Hetro, A. D., et al. *Biotechnol. Bioeng.*, 64, 2, 250 (1999); Lejeune, K. E., et al. *Biotechnol. Bioeng.*, 54, 105, (1997); LeJeune, K. E. and Russell, A. J. *Biotechnol. Bioeng.*, 51, 450 (1996). In general, these surfactants were used in an attempt to optimize the performance of the polyurethane sponge product in a particular application. For example, the studies of Havens and Rase were focused upon using the resultant polymers as column packing material and as adsorbent sponges to decontaminate pesticide spills. The studies reported varying surfactant hydrophobicity could produce polymers that were better suited for a particular application. The enzyme concentration/loading employed in the studies of Havens and Rase and the other studies was quite low (in general, well below 0.1 weight percent of the polymer).

It is desirable to develop enzyme containing polymers and methods of synthesis of such polymers in which enzyme loading and enzyme activity are improved.

SUMMARY OF THE INVENTION

The present inventors have discovered that certain surfactants not only enable control of polyurethane physical properties/morphology, but enhance the activity of immobilized enzymes at relatively high enzyme loading. As used herein, the term "enzyme" refers to a protein that catalyzes at least one biochemical reaction. A compound for which a particular enzyme catalyzes a reaction is typically referred to as a "substrate" of the enzyme. Enzymes typically have molecular weights in excess of 5000.

In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

In one aspect, the present invention provides a method of increasing loading of active enzyme immobilized in a polyurethane polymer including the steps of:

synthesizing the polyurethane polymer in a reaction mixture containing water and enzyme; and including a sufficient amount of a surfactant in the reaction mixture to increase enzyme activity at an enzyme loading (as compared to a polymer of the same enzyme loading synthesized without surfactant).

As used herein, the term "surfactant: refers generally to a surface active agent that is reduces the surface tension of a liquid (water, for example) in which it is dissolved.

Preferably, the surfactant is nonionic and comprises between 0.5 to 5.0 weight percent of the aqueous component of the mixture. In the synthesis of the polyurethanes of the present invention, urethane prepolymers were mixed with water. The aqueous component of the reaction mixture included water, enzyme, surfactant and buffer salts. The weight percent surfactant in the aqueous component is thus calculated by dividing the weight of the surfactant by the weight of the entire aqueous component and multiplying the result by 100%. The enzyme loading in the present invention can be greater than approximately 0.1 percent by weight of the polyurethane polymer (weight of enzyme/[weight of enzyme-containing polymer product]*100%) while retaining substantial enzyme activity. Relatively high activity is maintained even when the enzyme loading is greater that approximately 0.5 percent by weight of the polyurethane polymer. Indeed, relatively high activity is maintained even when the enzyme loading is greater that approximately 1 percent by weight of the polyurethane polymer.

The polyurethane polymers of the present invention preferably include at least one of an oxidoreductase, a transferase, a hydrolase, a lyase, an isomerase or a ligase. Examples of enzymes suitable for use in the present invention include, but are not limited to, a lipase, a peroxidase, a tyrosinase, a glycosidase, a nuclease, a aldolase, a phosphatase, a sulfatase, or a dehydrogenase.

More than one type of enzyme are easily co-immobilized within the polyurethane polymer. The enzymes can be within the same class (for example, two hydrolases) or a within different classes of enzyme.

In another aspect, the present invention provides a polyurethane polymer containing an enzyme loading of more than approximately 0.1 weight percent. The polyurethane polymer is synthesized in the presence of a sufficient amount of a surfactant (preferably, nonionic) to increase enzyme activity at the enzyme loading of the polymer (as compared to the case when no surfactant is used).

In still another aspect, the present invention provides a method of improving enzymatic activity of a polyurethane polymer synthesized with an enzyme loading of more than approximately 0.1 weight percent. The method includes the step of:

adding a sufficient amount of a surfactant (preferably, nonionic) to during synthesis of the polyurethane polymer to increase enzyme activity at the enzyme loading.

The polymers and methods of the present invention provide enhanced enzyme activity retention as the enzyme loading or enzyme content of such polymers is increased (for example, to above approximately 0.1 weight percent of the polymer). Relatively large quantities of enzymes are immobilized within the polymers of the present invention while retaining a significant portion of the native enzyme specific activity.

DETAILED DESCRIPTION OF THE INVENTION

The enzyme-containing polyurethane polymers of the present invention can, for example, be synthesized by reaction of relatively hydrophilic polyurethane prepolymer with aqueous solution to produce a urethane foam. The polyurethane prepolymers used in the present studies were urethanes that were capped (that is, functionalized at chain ends) with multiple isocyanate functionalities. Prepolymers containing multiple isocyanate functionalities have the ability to form chemical crosslinks upon reaction with a diol or water. Water reacts with isocyanates, initiating a foaming reaction in which a carbamic acid intermediate is formed. The carbamic acid quickly degrades to an amine and evolves $CO_2$. The carbon dioxide bubbles through the highly viscous reacting polymer solution, creating a porous foam structure. Because amines readily react with isocyanates, a multifunctional prepolymer in aqueous solution results in a crosslinked polyurethane matrix.

Figure 1:
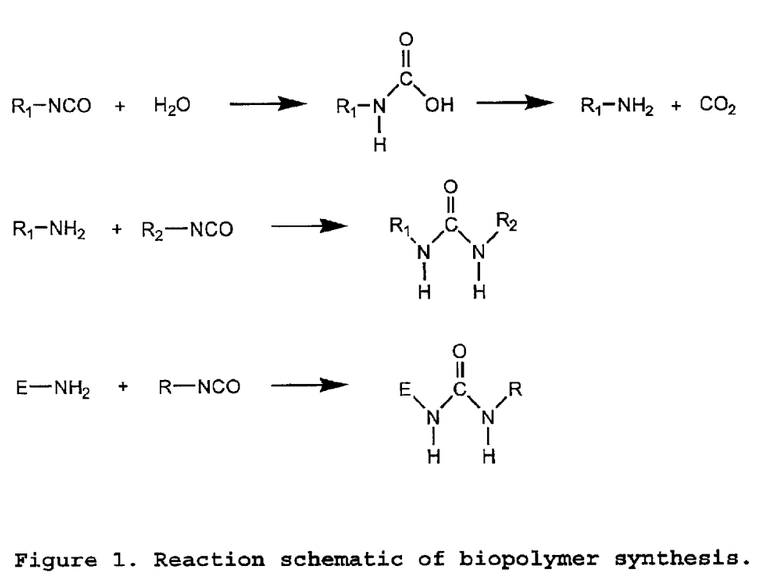
FIG. 1 illustrates an embodiment of a synthetic scheme synthesis of enzyme-containing polymers.

Because the vast majority of enzymes are most active in aqueous solution, water not only serves to initiate the prepolymeric reaction, but also provides a route to deliver an enzyme to the reaction. Proteins such as enzymes have many amine groups present via lysine residues and can readily react with isocyanate functionalities to form a crosslinked polymer-protein network through multi-point attachments of the enzyme and polymer. A schematic of the reactions occurring in this process is illustrated in FIG. 1. In FIG. 1, $R_1$ represents a prepolymer molecule (for example, having a molecular weight of approximately 300 to approximately 10,000) having multiple isocyanate functionalities/groups. $R_2$ and R represent other prepolymer molecules with isocyanate functionalities. E represents an enzyme with a reactive amine functionality present via lysine residues and at the N-terminus of the protein.

It is believed that the surfactants used in synthesis of enzyme-containing polyurethane polymers of the present invention enhance the activity of biocatalytic polymers when the enzymatic content of the composite materials is sufficiently high to overwhelm the capacity of the polymer to provide the enzyme incorporated therein with sufficient access to bind substrate or to release product at a rate equivalent to the maximum achievable catalytic rate. In that regard, several studies of the present invention have demonstrated that polymers with excessive enzyme content are diffusionally limited in their ability to catalyze reactions. It is believed, that the use of certain surfactants over a range of concentrations eliminates the diffusional limitations imposed by a polymeric superstructure within which relatively large amounts of enzyme have been incorporated.

Experimental Procedures

1. Enzyme Polymer Synthesis

As known in the art, variation of reaction conditions affects both the physical properties polyurethane foams and the degree of enzyme-foam interaction. Described below is a typical procedure for biopolymer synthesis used in the present studies. Initially, 4 ml of pH 7.8 Tris buffer (10 mM) containing a specific surfactant at a particular concentration (approximately 0 to 8 weight percent in the studies of the present invention) were placed into a narrow cylindrical mixing vessel. Subsequently, an enzyme solution (for example approximately 1 ml of 1.5 mg/ml urease in the same buffer, for example) was added. Finally, approximately 4 ml of Hypol prepolymer, available from Hampshire Chemical Corp., a subsidiary of Dow Chemical Company, (preheated to 30° C. to limit handling problems resulting from high viscosity) were added to the mixture. The solutions was then intimately mixed. During the initial "cream" period, the solution was injected into a cylindrical mold where it rose and then set within 2 to 5 minutes. Polymer synthesis was complete in less than 10 minutes. The $CO_2$ evolved during the reaction of water and isocyanate lifted, the foam to a final volume of approximately 50 to 60 ml.

After the initial 10 minute "set-up" time, foam samples were treated in several ways. Some foam samples were immediately sealed in vials, while others were pre-rinsed. Bulk foam samples were typically placed in a fume hood or lyophilizer to facilitate the removal of residual water and $CO_2$ still present from the reaction. Foams were stored under a wide range of conditions until being assayed for enzyme activity.

The mixing system used in the present studies required 30 to 40 seconds of mixing at 2500 rpm to create a high quality foam with Hypol 3000, a toluene di-isocyanate based prepolymer. The mixing system included an oar-shaped metal loop having a height of 3.2 cm and a diameter of 1.3 cm. Hypol 5000 (methylene bis(p-phenyl isocyanate) based), a more hydrophobic prepolymer, required additional mixing. Insufficient mixing can result in un-reacted residual prepolymer dispersed within a dense hard mass of polyurethane. Overmixing does not allow the evolving $CO_2$ to act in lifting the foam. Properly mixed foam will typically increase approximately six-fold in volume throughout the course of the reaction.

In one embodiment of the present invention, an aqueous solution of enzymes and surfactant was contacted with an isocyanate-based prepolymer under sufficient agitation to initiate reaction. The enzyme can, for example, be added as a freeze-dried powder or aqueous solution that is either pure or impure. The term "impure" a used herein refers generally to enzymes containing, for example, other proteins/enzymes and biological molecules. Virtually any enzyme or combination of enzymes can be co-immobilized within the same polymer in the present invention.

In model studies of the present invention, enzyme-containing polymers were synthesized both with and without a series of surfactants. Enzymes incorporated into the polymers of the present invention included, for example, organophosphorus hydrolase (OPH), organophosphorus acid anhydrolase (OPAA), butyrylcholinesterase (BChE), urease, and subtilisin carlsberg. The benefit of using certain surfactants in the synthesis of the enzyme-containing polymers of the present invention was demonstrated with in series of kinetic experiments discussed below.

2. Increasing Enzyme Activity in Highly Loaded Polymers Through the Use of Surfactants Using the procedures described above for polymer synthesis, enzyme-containing polymers were synthesized both with and without the use of surfactants. For example, subtilisin carlsberg and urease enzymes were individually incorporated within polyurethane polymers over a range of enzyme concentrations from approximately 10 $\mu$g to approximately 20 mg enzyme per gram polymer (that is, approximately 0.001 to approximately 2% by weight. Multiple polymers were synthesized at each enzyme concentration, some with the use of 1 weight percent Pluronic F-68 non-ionic surfactant present and some without surfactant. The polymers were placed in a fume hood for 12 hours after synthesis to facilitate the removal of residual water and $CO_2$ before their catalytic activity was assessed.

Figure 2:
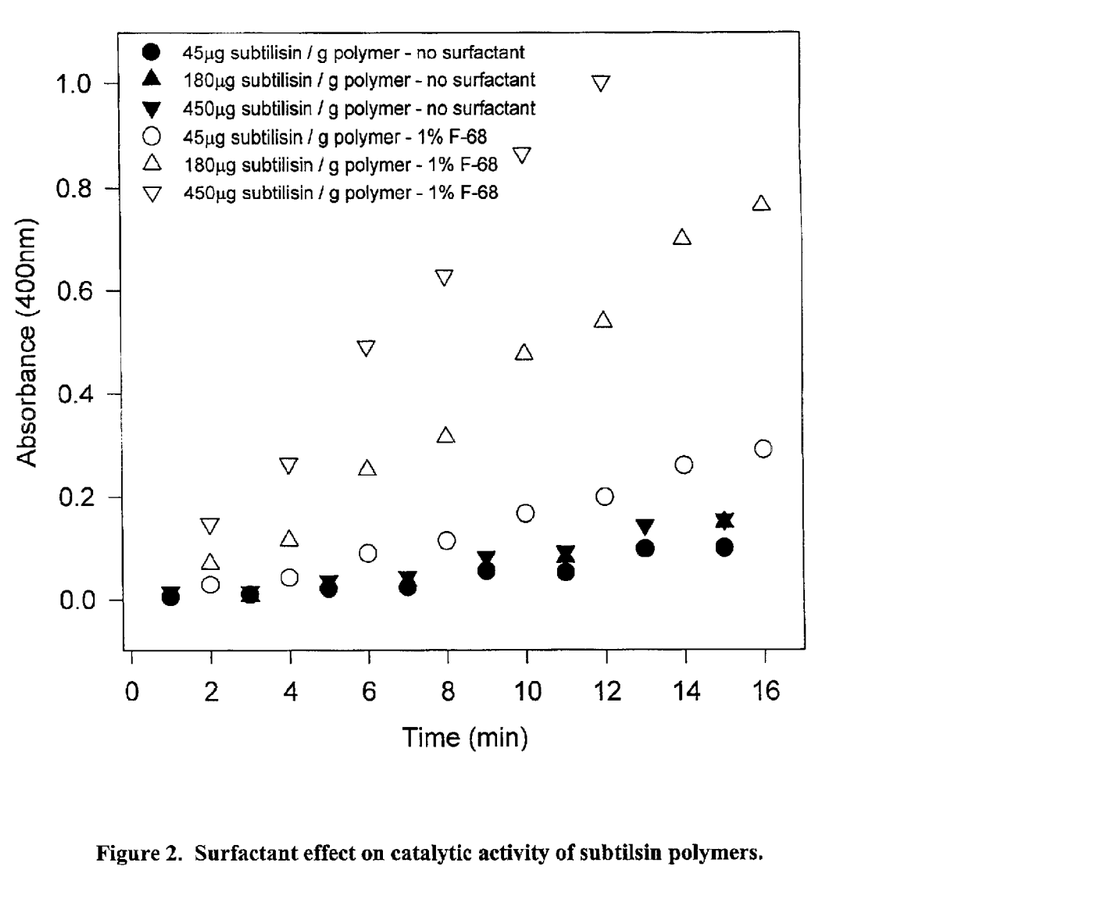
FIG. 2 illustrates the effect of using surfactant in the synthesis of subtilisin-containing polyurethane polymers.

Subtilisin-containing polymers were assayed for their hydrolytic activity on N-succinyl-ALA-ALA-PRO-PHE p-nitroanilide in 10% MeOH/50 mM Tris buffer (pH 8.0) solutions. Substrate hydrolysis was monitored with the use of a spectrophotometer. Reaction rates were determined by placing polymer samples (100 mg) within 10 ml substrate solutions and taking and subsequently replacing aliquots from the reacting system at regular intervals. FIG. 2 illustrates the benefit achieved by including surfactant within the polymer formulation. Without the addition of surfactants during the polymer synthesis, very little if any benefit is incurred by increasing the enzyme content within the polymers, whereas those polymers synthesized in the presence of surfactant exhibited activity levels which were closely related to enzyme content.

Figure 3:
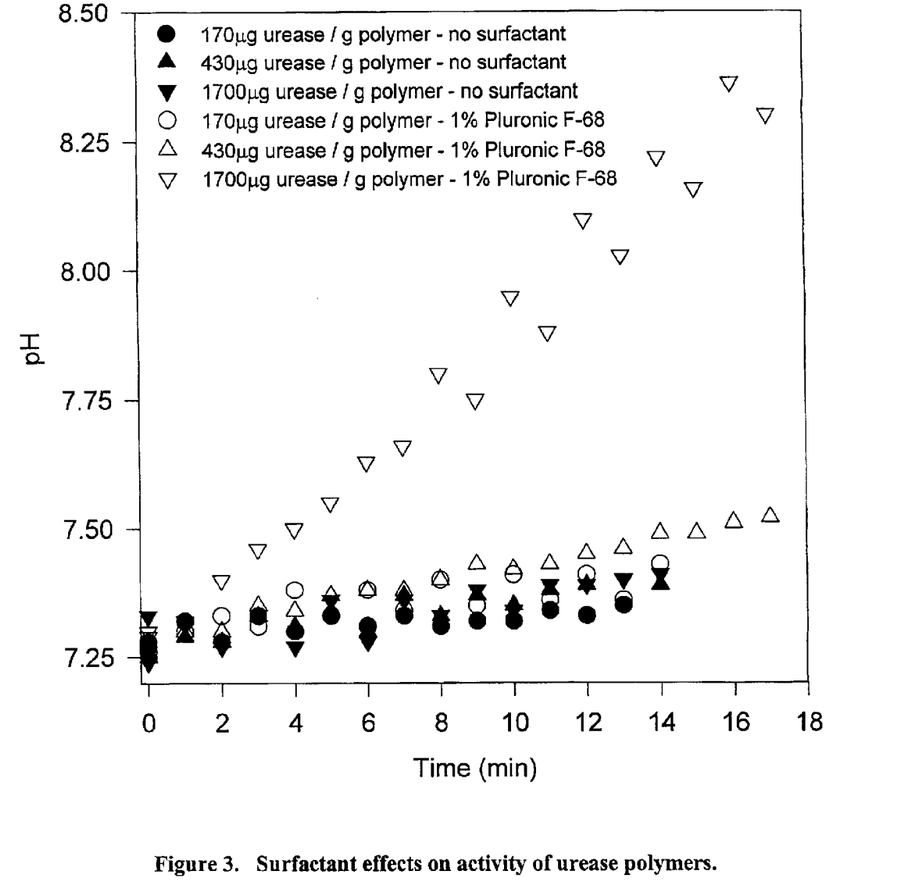
FIG. 3 illustrates the effect of using surfactant in the synthesis of urease-containing polyurethane polymers.

The activity of urease polymers (150 mg samples) was assayed in 300 mM urea within 10 mM Phosphate buffer at pH 7.25 (15 ml). Urea hydrolysis was assessed by monitoring solution pH, since urea hydrolysis causes a corresponding increase in pH. FIG. 3 shows that there are no significant diffusional limitations present at low enzyme concentration. The rates of reaction with or without surfactant are essentially identical when the urease content of the polymer is low (see Table 1 for rate data). The rate of catalysis is proportional to enzyme concentration in the presence of surfactant. However, the absence of surfactant is believed to result in diffusional limitations within the system. Apparent catalytic activity was found to have very little dependence upon enzyme loading when surfactants are not utilized in polymer synthesis.

TABLE 1

Rate data for urease-polymer assays.

| Enzyme loading in polymer ($\mu$g urease/g polymer) | Polymers synthesized with surfactant Reaction Rate ($\Delta$pH/min)*$10^3$ | Polymers synthesized without surfactant Reaction Rate ($\Delta$pH/min)*$10^3$ |
|---|---|---|
| 170 | 8.2 | 6.4 |
| 430 | 15.0 | 8.7 |
| 1700 | 63.0 | 9.8 |

Diffusional limitations for other enzymes (including organophosphorus hydrolase, organophosphorus acid anhydrolase, and butyrylcholinesterase) have also been measured.

3. Surfactant Concentration

The amount of surfactant present during polymer synthesis was found to affect the retention of enzyme activity in the enzyme-containing polymers of the present invention. In the limit as surfactant concentration approaches zero, the resulting material exhibits the same polymer properties and subsequent diffusional limitations present when no surfactant is employed. The effect of the amount of surfactant used was studied by synthesizing biocatalytic polymers with sufficient enzyme loading to cause diffusional limitation in the absence of surfactant. Nearly identical synthetic procedures were also carried out for polymers in which Pluronic F-68 surfactant content was gradually increased to near its solubility limit in water (7.5%).

Figure 4:
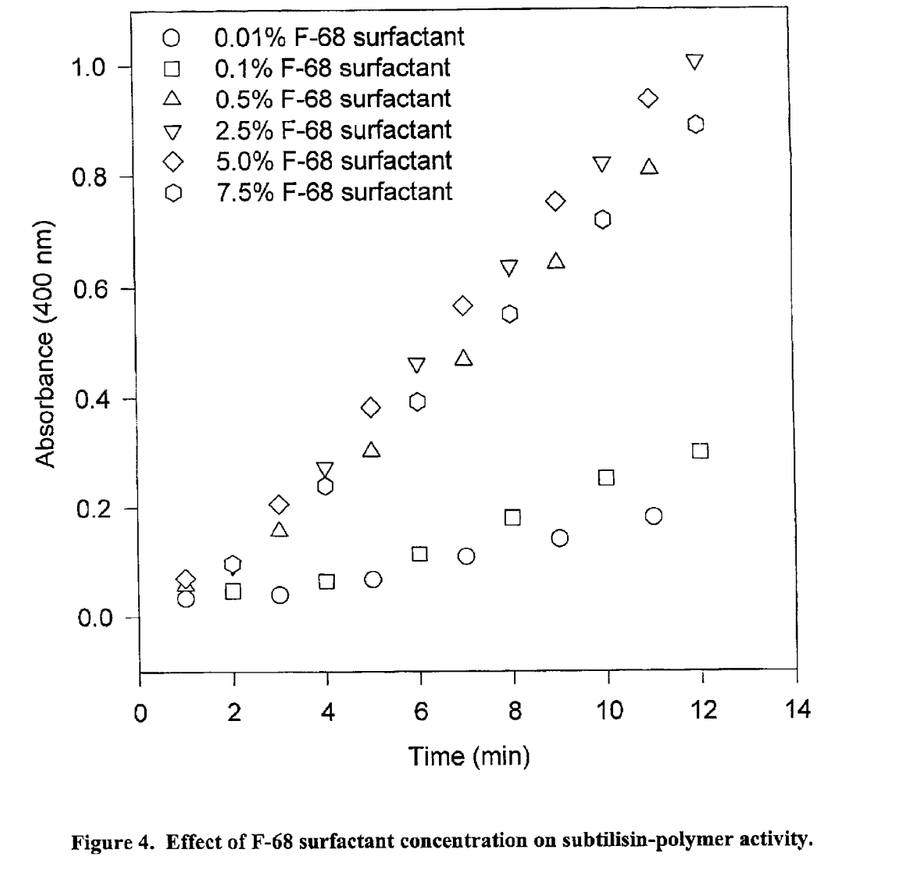
FIG. 4 illustrates the effect of surfactant concentration upon the catalytic activity of polymer containing subtilisin carlsberg.

Subtilisin-containing polymers were synthesized with an enzyme loading of approximately 250 $\mu$g enzyme per gram polymer. This degree of loading is believed to be sufficient to incur diffusional limitations within polymers not formulated for high enzyme loading (see FIG. 2) through the use of sufficient surfactant during synthesis. FIG. 4 illustrates a study of the effect of surfactant concentration upon the rate of catalysis observed for subtilisin-polymers (100 mg) having an enzyme loading of 250 $\mu$g enzyme per gram polymer that were assayed against N-succinyl-ALA-ALA-PRO-PHE p-nitroanilide in 10% MeOH/50 mM Tris buffer (pH 8.0) solutions (10 ml). Surfactant concentrations of less than 0.5 weight percent of the aqueous synthesis component were found to be insufficient to overcome the diffusional limitations imposed at this level of enzyme loading. The data indicate that an "optimum" surfactant concentration exists between approximately 0.5 and approximately 5.0 weight percent. The data of Table 2 indicates that increasing surfactant concentration beyond the optimum concentration did not further improve activity. It is possible that diffusional limitations were overcome at the enzyme loading studied at the lower surfactant concentration.

TABLE 2

Rate data for urease-polymer assays.

| Surfactant concentration used in polymer synthesis (wt % aqueous phase) | Observed Rate ($\Delta Abs_{400nm}$/min)*$10^2$ |
| --- | --- |
| 0.01 | 1.5 |
| 0.1 | 2.7 |
| 0.5 | 7.7 |
| 2.5 | 9.1 |
| 5.0 | 8.8 |
| 7.5 | 7.9 |

4. The Nature of the Surfactant

The above studies demonstrated that retention of enzyme activity is improved through the use of surfactants in polymer synthesis. There are, however, many types of surfactants which one might envision using to synthesize polymers. The broadest classification of surfactants is based upon the charge of the head group. The available surfactant pool includes of anionic, cationic, and non-ionic surfactants. In several studies, two representative surfactants were selected from each group and employed in polymer synthesis at a loading of 1 weight percent of the aqueous component of the synthesis mixture. Polymers without surfactant and without enzyme were synthesized as controls for the activity assays.

Subtilisin was used as a model enzyme in these studies. The procedures described above were employed to synthesize the enzyme polymers (200 µg subtilisin/gram polymer). Anionic (lauryl sulfate, octyl sulfate), cationic (cetylpyridinium chloride, dodecyltrimethylammonium bromide) and non-ionic (Pluronic™ F-68 available from BASF Corp., Mount Olive, N.J. and Tween™ 20 available from ICI Americas, Wilmington Del.) surfactants were each used in synthesizing individual enzyme polymer samples. The polymers were exposed to open air in a fume hood for several hours before assay to facilitate the removal of residual water and $CO_2$.

Figure 5:
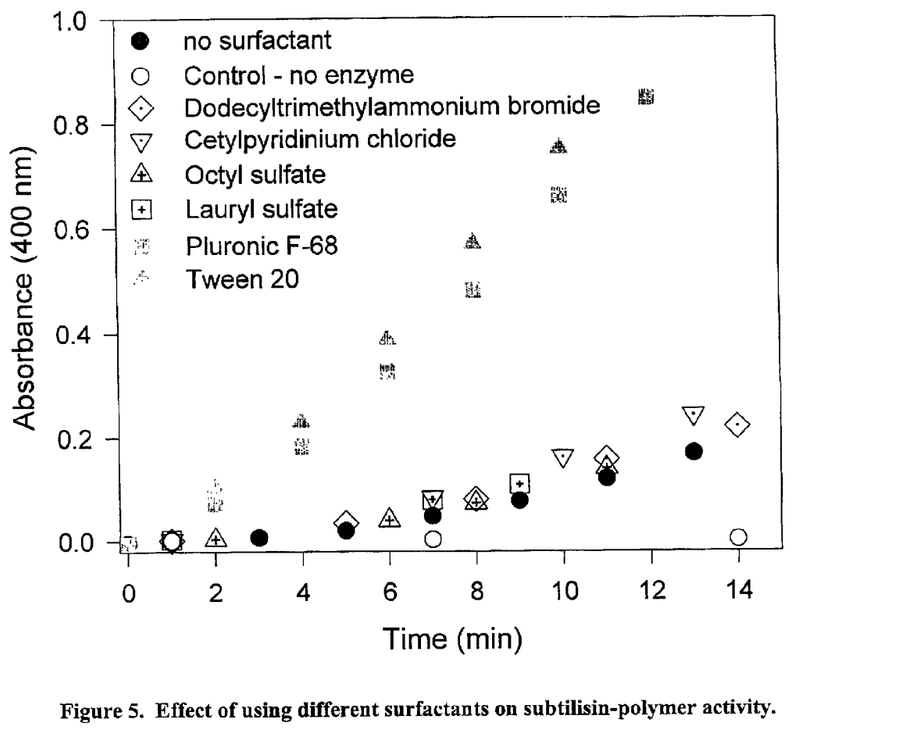
FIG. 5 illustrates a study of the utility of non-ionic surfactants in polymer synthesis as compared to surfactants that are cationic or anionic in nature.

The resulting polymers were assayed for their hydrolytic activity on N-succinyl-ALA-ALA-PRO-PHE p-nitroanilide in 10% MeOH/50 mM Tris buffer (pH 8.0) solutions. Substrate hydrolysis was monitored with the use of a spectrophotometer at 400 nm. Reaction rates were determined by placing polymer samples (100 mg) within 10 ml substrate solutions. The data of FIG. 5 indicate that, while polymers synthesized without surfactant or with cationic or anionic surfactants have appreciable catalytic activity (compared to the corresponding polymer, without enzyme), one preferably uses non-ionic surfactant(s) in polymer synthesis to maximize the retained activity of the enzyme immobilized therein. Table 3 further illustrates this phenomenon. The relative reaction rates are ratios based upon the catalytic rates achieved when no surfactant is employed.

TABLE 3

Relative catalytic rates when employing different surfactants in subtilisin polymer synthesis.

| Surfactant Classification | Surfactant used in polymer synthesis (1 wt % of aqueous phase) | Relative Reaction Rates |
| --- | --- | --- |
| | None | 1.0 |
| Anionic | Lauryl sulfate | 1.0 |
| | Octyl sulfate | 1.1 |
| Cationic | Cetylpyridinium chloride | 1.5 |
| | Dodecyltrimethylammonium bromide | 1.3 |
| Non-ionic | Pluronic F-68 | 5.8 |
| | Tween 20 | 6.2 |

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of increasing loading of active enzyme immobilized in a polyurethane polymer, the method comprising the steps of:

synthesizing the polyurethane polymer in a reaction mixture containing water and enzyme wherein an enzyme loading of the polyurethane polymer is greater than approximately 0.5 percent by weight of the polyurethane polymer; and including a sufficient amount of a surfactant in the reaction mixture to increase enzyme activity at the enzyme loading.

2. The method of claim 1 wherein the enzyme loading is greater than approximately 1 percent by weight of the polyurethane polymer.

3. The method of claim 1 wherein enzyme immobilized in the polyurethane polymer includes at least one of an oxidoreductase, a transferase, a hydrolase, a lyase, an isomerase or a ligase.

4. The method of claim 1 wherein enzyme immobilized in the polyurethane polymer includes at least one of a protease, a lipase, a peroxidase, a tyrosinase, a glycosidase, a nuclease, a aldolase, a phosphatase, a sulfatase, or a dehydrogenase.

5. The method of claim 1 wherein at least two species of enzyme are co-immobilized within the polyurethane polymer.

6. The method of claim 5 wherein the two species of enzyme are within the same class of enzyme.

7. The method of claim 1 wherein the surfactant comprises between 0.5 to 5.0 weight percent of the aqueous component of the mixture.

8. The method of claim 1 wherein the enzyme is a hydrolase and the surfactant is nonionic.

* * * * *

UNITED STATES PATENT AND TRADEMARK OFFICE
CERTIFICATE OF CORRECTION

PATENT NO.    : 6,759,220 B1
DATED         : July 6, 2004
INVENTOR(S)   : Keith E. Lejeune and Alan J. Russell It is certified that error appears in the above-identified patent and that said Letters Patent is hereby corrected as shown below:

Title page,
Item [56], References Cited, OTHER PUBLICATIONS, "van de Velde, et al.," reference, change "Coimmobilizatiojn" to -- Coimmobilization --.

Signed and Sealed this

Sixteenth Day of November, 2004

JON W. DUDAS
*Director of the United States Patent and Trademark Office*